(12) United States Patent
Taylor, Jr. et al.

(10) Patent No.: US 6,282,950 B1
(45) Date of Patent: Sep. 4, 2001

(54) METHOD AND APPARATUS FOR TESTING THE BOND STRENGTH OF MATERIALS

(75) Inventors: Myron Eugene Taylor, Jr., Brookeville; Jon Allen Massey, Monrovia, both of MD (US)

(73) Assignee: M. E. Taylor Engineering, Inc., Brookeville, MD (US)

( * ) Notice: Subject to any disclaimer, the term of this patent is extended or adjusted under 35 U.S.C. 154(b) by 0 days.

(21) Appl. No.: 09/640,656

(22) Filed: Aug. 18, 2000

(51) Int. Cl.[7] .................................................. G01B 21/08
(52) U.S. Cl. ............................................ 73/150 A; 73/827
(58) Field of Search ............................. 73/150 R, 150 A, 73/827, 835

(56) References Cited

U.S. PATENT DOCUMENTS

| 4,491,014 |   | 1/1985  | Seiler, Jr. ........................ | 73/150 A |
|-----------|---|---------|----------------------------------|----------|
| 4,567,758 |   | 2/1986  | Fisher et al. ..................... | 73/150 A |
| 4,586,371 |   | 5/1986  | Ivie et al. ........................ | 73/150 A |
| 4,715,718 | * | 12/1987 | Evans .............................. | 356/446  |
| 4,729,070 |   | 3/1988  | Chiu ............................... | 362/33   |
| 4,831,264 | * | 5/1989  | Fujiwara .......................... | 250/372  |
| 4,871,921 | * | 10/1989 | Gurnee ............................ | 250/208  |
| 5,085,074 | * | 2/1992  | Notle et al. ...................... | 73/150 A |
| 5,176,028 |   | 1/1993  | Humphrey ........................ | 73/150 A |
| 5,323,952 | * | 6/1994  | Kato et al. ....................... | 228/102  |
| 5,671,634 |   | 9/1997  | Donovan .......................... | 73/150 A |

OTHER PUBLICATIONS

Advertising Brochure "P.A.T.T.I"®, Semicro Div., M. E. Taylor Engineering, Inc. (Published approx. Jan. 1999.
Operating Instructions—FO–150 (Lumina 1) Illuminator Chiu Technical Corp.

* cited by examiner

Primary Examiner—Max Noori
(74) Attorney, Agent, or Firm—Randall G. Erdley

(57) ABSTRACT

A method and apparatus for testing the bond strength of materials such as a coating (101) on a substrate (100) wherein a stub (102) is placed on the coating (101) with a light curable adhesive (114) therebetween, the stub having a threaded section extending upwardly and being made of light transparent material, or a material that is at least partly transparent, a high intensity light (111) is positioned over the stub and operated to irradiate the adhesive through the stub to cure the adhesive, after which a force is applied to the stub in a direction normal to the coating tending to separate the coating from the substrate and is measured to determine the amount of force required. The apparatus includes a stand off ring (23) positioned around the stub for supporting cylinder housing (1) in spaced relationship to the coating, the housing having a cavity therein formed by inner (7) and outer (3) walls and a lower plate for receiving piston (9) therein retained by reaction plate (14). Adapter (24) is threadedly connected (27) (105) to stub (102) and extends through hole (108) in the cylinder housing and hole (13) in the piston and threadedly engages (25)(18) the reaction plate so that fluid pressure fed by pressure source (31) to compression chamber (29) compresses piston (9) against the reaction plate and the housing against the stand off ring to apply the force through the adapter and stub tending to separate the coating in the test area from the substrate. The force is measured by gage (32).

15 Claims, 3 Drawing Sheets

METHOD AND APPARATUS FOR TESTING THE BOND STRENGTH OF MATERIALS

BACKGROUND OF THE INVENTION

This invention relates to the testing of bond strength of materials and more particularly to methods and apparatus for measuring and testing the strength of a bond between an element or a coating and a surface, body, or substrate to which the element or coating has been attached. In the case of a coating for example, this might be a protective coating, such as paint or metal cladding on an element which in use would be subject to corrosive environments, or simply oxidation. Another example would be metal cladding on a nuclear fuel element, Adhesion testers of the type of this invention for testing the bond strength of materials are shown and referred to in U.S. Pat. No. 4,567,758, to R. K. Fisher and & L. Fisher, the teachings of which are incorporated in their entireties herein by reference. This prior patent points out that although adhesion testers of this type have been made in various forms which operate in different ways they generally have four steps in common: (1) attaching a fastener to the material to be tested, (2) applying a tensile force to the fastener along an axis normal to the surface, (3) measuring the maximum tensile force required to cause bond failure, and (4) computing a relative measure of the bond strength by dividing the maximum tensile force by the area of the stressed surface of the failed bond. The Fisher patent then discusses major problems encountered in each of these steps and the manner in which these problems are overcome by the apparatus invention set forth in said patent.

However, there is an additional problem in carrying out step (1) in that an undesirable amount of time is necessary for curing of the adhesive such as epoxy or other suitable material, which is strong enough for the intended purpose for example, used to attach the fastener to the coating or layer to be tested. This delays the measuring and testing process and can be costly, particularly in a continuously operating system, such as in a production or assembly line, or where rigid time constraints are required to meet a predetermined schedule, for example.

Additional prior patents in the field of testing of bond strength of materials are discussed below. U.S. Pat. No. 4,586,371 shows an apparatus for testing the adhesive bond strength between a coating and a substrate using a piston and cylinder coupled to a dolley which is adhesively connected to the coating by cured epoxy. U.S. Pat. No. 5,176,028 shows an apparatus and method for testing bond strength of overlapped ends of substrate material to which adhesive has been applied to bond the ends together. The ends are pressed together with the bonding material between them by opposing press heads having heaters for heating the test samples during pressing for a predetermined time interval to assist in setting the bond material. The ends are then sheared apart and data is compiled representing the relationship between bonding strength development and temperatures, and between bond strength and bonding pressure. U.S. Pat. No. 5,671,634 shows an apparatus and method for testing adhesion quality of coatings applied onto a substrate wherein a pulling element has a face at one end which is joined to the coating by an adhesive disk preferably made of cyanoacrylate having a thermosetting temperature of about 25 C and a curing time of 15–30 minutes. A piston and cylinder device connected to the pulling element operates to pull the latter and the disk in a direction normal to the coating tending to separate the coating from the substrate. Prior to the pulling operation the assembly is subjected to heat to set the adhesive disk.

It is also known to use light curable adhesives for securing various elements together, such as a cyanoacrylate material known as "Loctite"4304.

These prior art patents all have the same time delay problems pointed out above in that considerable time may be lost in carrying out the process due to the curing time required for the adhesive. The present invention provides a solution to these problems.

It is also known to use high intensity light devices for various purposes, such as described in U.S. Pat. No. 4,729,070, powered by a compatible lamp source to provide the desirable light intensity.

SUMMARY OF THE INVENTION

It is a principal object of the invention to provide a method and apparatus for reducing the time required to conduct a measuring and testing operation for determining the bond strength of materials such as coatings, for example. It is a further object of the invention to provide a method and apparatus for eliminating the curing time previously required for adhesives used in joining pulling devices to coatings being tested to determine the strength of bonds between the coatings and substrates to which the coatings have been applied. It is a still further object of the invention to provide a method and apparatus for measuring the in-situ bond strength of materials which is adaptable to a wide variety of materials.

It is a further object of the invention to provide a method and apparatus for producing a bond between the adhesive joining pulling devices to coatings being tested and the coatings which has a substantially greater strength than heretofor known.

It is another object of the invention to provide a method and apparatus for measuring the bond strength of materials which can be directly calibrated and verified.

It is a further object of the invention to provide a method and apparatus for measuring the bond strength of materials which is inherently self-aligning, and is small, inexpensive, and suitable for field service.

It is still another object of this invention to mitigate friction at all seal boundaries and produce a supplemental force capable of further compensating for residual losses.

The foregoing and other objects of the invention are achieved by the method described herein including the steps of providing a substrate having a coating thereon to be tested for bond strength between the coating and the substrate, connecting a pulling device to a section of the coating by an adhesive that is curable by irradiation with light, irradiating the adhesive with light to cure the adhesive and produce a strong bond between the pulling device and the coating, exerting a force on the pulling device in a direction substantially normal to the coating tending to strip the coating from the substrate, measuring the force required to strip the coating from the substrate, and computing a relative measure of the bond strength by dividing the maximum pulling force by the stressed surface area of the failed bond. The method of this invention may also include additional steps of providing an instant pull stub made of light transparent material, or a pull stub that is at least partly transparent to light, applying the adhesive to connect the instant pull stub to the coating by the adhesive, irradiating the adhesive with light,preferably high intensity light through the stub, connecting the pulling device to the stub, and supporting and guiding the pulling device during the force exerting step.

The above and other objects of the invention are further achieved by the apparatus described herein including a housing having a longitudinal axis normal to predetermined area, preferably a central area, on its upper transverse surface, a cavity formed in the upper surface including the central area, the cavity having a centroid of transverse area lying on the longitudinal axis of the housing, a fluid seal member, or piston, received in the cavity, a reaction plate covering the upper surface of the housing and cavity, and a source of pressurized fluid communicating with the cavity and the inner surface of the seal member forming one side of the cavity and a fluid pressure sensing device. Further in accordance with the preferred embodiment of the invention a stub member of light transparent material, or a stub member that is at least partly transparent to light, is attachable at its lower end to the coating on the substrate by light curable adhesive and has a connecting part at its upper end for connecting to the lower end of a coupler or adapter. A stand off ring has a central aperture for receiving the adapter in guiding relationship and has upper and lower faces, the lower face engaging in use the upper surface of the coating and the upper face engaging the lower surface of the housing for supporting the housing. An aperture is provided through the lower surface of the housing and another aperture is provided through the fluid seal member for receiving the upper part of the adapter which is connected to the reaction plate by threaded engagement therewith, for example, the stub and adapter each having a central longitudinal axis extending coaxially with the longitudinally axis of the housing, so that when pressure is applied to a chamber in the cavity between the fluid seal member, or piston, and the housing the fluid seal member forces the reaction plate in a direction away from the chamber, thereby drawing the adapter and stub member in a direction normal to the coating tending to strip the coating from the substrate in the performance of the test for bond strength. A light source, preferably high intensity light source, is provided for irradiating the adhesive through the stub after the stub has been positioned on the coating with the adhesive therebetween. A cut off ring may also be used by placing it on the stub with its lower end in contact with the adhesive or the coating about the stub prior to energizing the light source.

BRIEF DESCRIPTION OF THE DRAWINGS

The invention will now be described in greater detail with reference to the accompanying drawings wherein.

DETAILED DESCRIPTION OF THE PREFERRED EMBODIMENT

Figure 1:
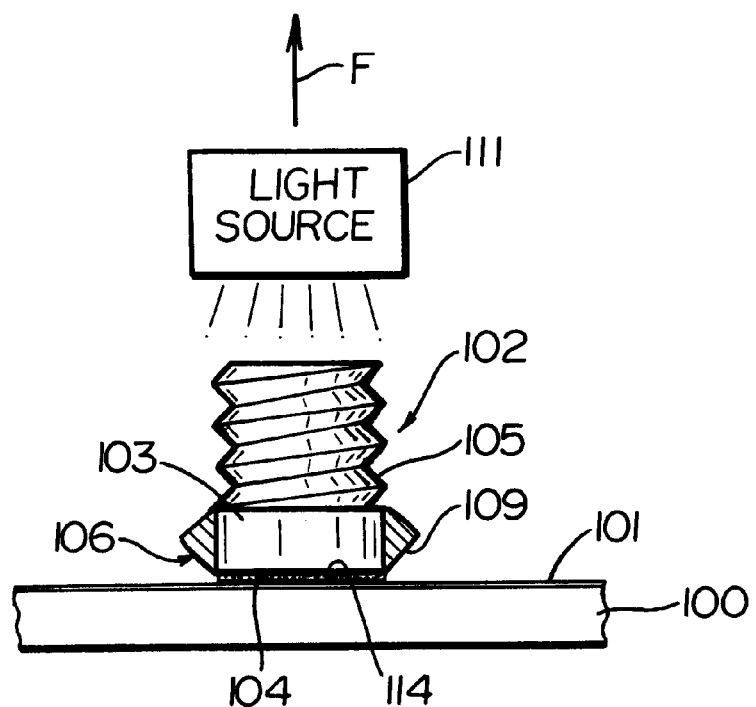
FIG. 1 is a schematic illustration showing the method of carrying out the invention.

FIG. 1 generally schematically illustrates the method of this invention for testing the bond strength of coating 101 which has been applied to the upper surface of a substrate 100. As shown and described in U.S. Pat. No. 4,567,758, referred to above, a threaded stub is bonded to the surface of a coating to be tested for bond strength, the apparatus of the patent is then connected to the stub and a force is applied normal to the coating surface by the apparatus. In the preferred embodiment of the instant invention the stub 102 is mad e of a light transparent material such as "Lexan", a polycarbonate resin product of the General Electric Co. Preferably the lower surface 104 of the lower section 103 of the stub is coated with a light curable adhesive 114, such as "Loctite" 4304, . Alternatively the adhesive can be applied to the surface of the coating or to both the stub and the coating. As shown in FIG. 1 a light, preferably a high intensity light, is positioned over the upper end of the stub and is focused to transmit light energy through the stub which guides the light to irradiate the adhesive 114 to produce the curing thereof and firmly connect or bond the stub to the coating. It has been found that the preferred high intensity light source is a commercial product known as a ring light of the type shown in U.S. Pat. No. 4,729,070, powered by a compatible lamp house, or power source to provide and control the desired intensity of the light. The light is energized for about 60 seconds total, or until the adhesive is completely polymerized and cured. The light 106 is then removed, whereafter a force F is applied to the stub in a substantially normal direction to the coating surface to pull the stub and thereby the coating from the substrate. The amount of force required to separate the stub from the coating, or to determine a maximum desired bond strength prior to destructive testing, is measured by a suitable gage, and the force is divided by the area of the surface being tested to determine the strength of the bond in psi.

In a further embodiment of the method of this invention, an adapter 24 is threadedly connected to the upper threaded section 105 of the stub by cooperating screw thread 27, for example, such as shown in FIGS. 2–6, and the adapter is supported and guided by a stand off ring 22 during the application of force to pull the stub which pulls the coating from the substrate to assure that the force is evenly applied over the area of the lower or bonded face of the stub to obtain maximum accuracy of the test.

Figure 7:
FIG. 7 is an enlarged elevational view of the cut off ring shown in FIG.2.

In another embodiment of this method a cut off ring 106 (see FIG. 7) having a short tapered section 108 and a long tapered section 109 is fitted onto the stub carefully to avoid moving the 5tub laterally after the stub is positioned on the coating with the adhesive between them and prior to the irradiation step. The cut off ring is positioned so that the lower edge 110 of the long tapered section 109 is in contact with the sample. The cut off ring thus controls the flow of the adhesive to substantially center and retain it to the area of the lower end 104 of the stub. With the cut off ring in position, the light is energized to irradiate and polymerize the adhesive for about 30 seconds. The light is then cut off, the cut off ring is gently removed by rotating it, for example, and the light is again applied focusing it at the base of the stub to obtain maximum light intensity for about 30 seconds or until the adhesive is completely cured. The total time for polymerization of the adhesive will vary depending on surface texture, color, and reflectance. It has been found that about 60 seconds is sufficient. The cut off ring is preferably plastic.

The above method has been found to be useful for most applications and to produce bond strength of the adhesive greater than 3000 psi,which is substantially greater than heretofor known for cyanoaccylate adhesives used in other methods and apparatus for testing bond strength of materials joining coatings to substrates, for example.

Figure 8:
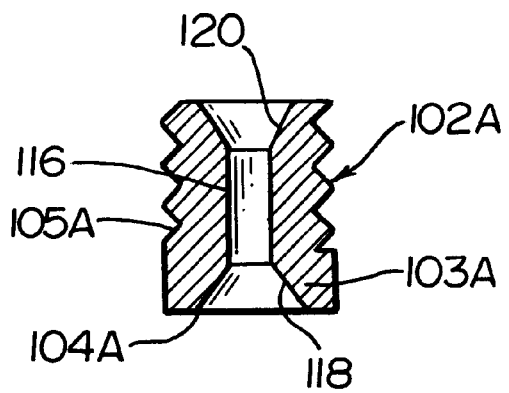
FIG. 8 is a cross-sectional view of a modified stub member.
Figure 6:
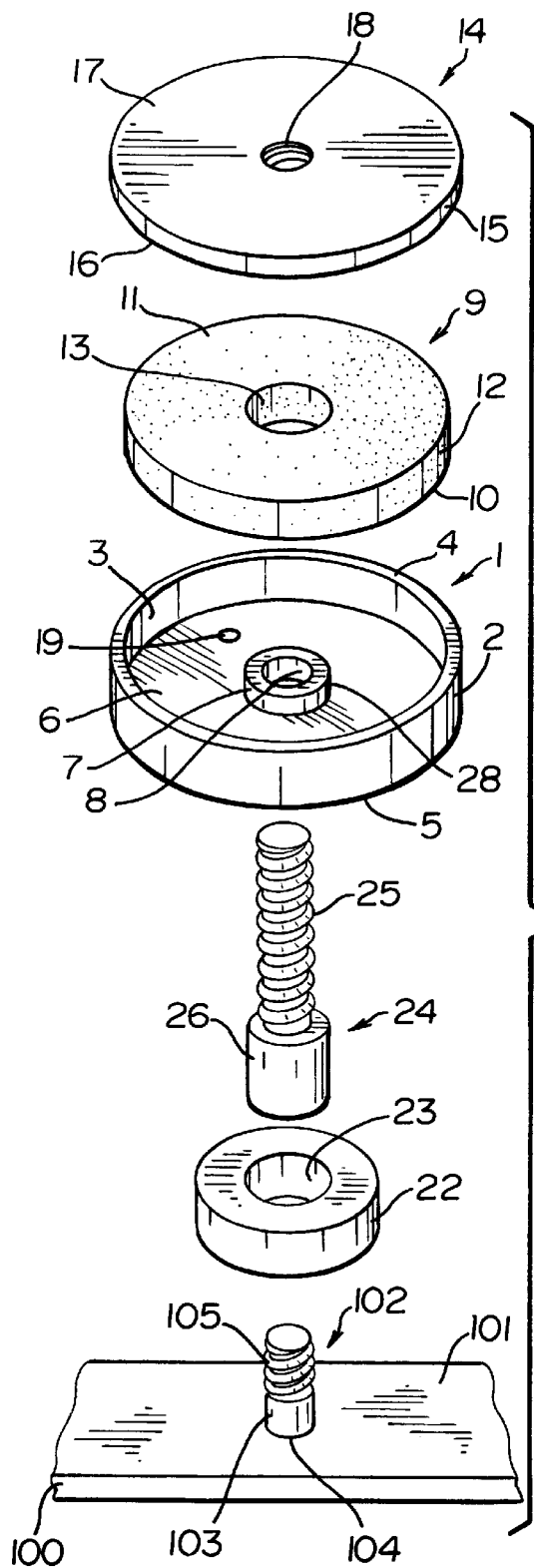
FIG. 6 is an enlarged elevational view of the adapter shown in FIG.2.
Figure 6:
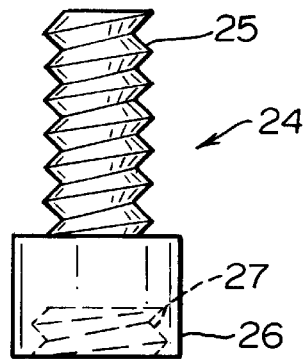
Figure 5:
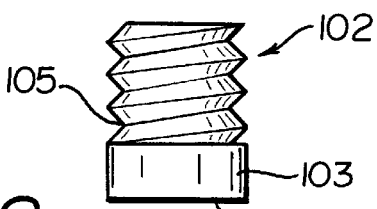
FIG. 5 is an enlarged elevational view of the pull stub.

In a modified embodiment of the stub member, shown in FIG. 8, the stub can be made of metal, such as aluminum for example, through which a bore 116 is provided for the insertion of the adhesive therethrough to the interface between the stub and the surface of the coating in the test area thereon. Conically shaped sections 118 and 120 are preferably provided at both ends of bore 116 to assist in providing even flow of the adhesive through the stub and to enhance the strength of the stub during the pulling step. The adhesive is transparent and therefor conducts and guides the light applied by light source 111 to carry out the irradiation step of the method of this invention.

Figure 2:
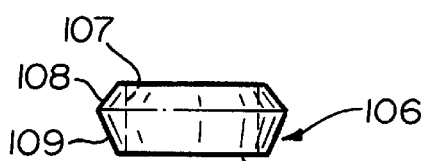
FIG. 2 is an exploded perspective view of the preferred embodiment of the apparatus of the invention and an exemplary showing of the manner in which the method of the invention is carried out.

The apparatus of the invention as shown in FIGS. 2~7 will now be described. Stub 102 is shown in FIG. 2 bonded by adhesive 114, as described above, at its lower end 104 to coating 101 on substrate 100 in position for placement thereon of the stand off ring 22 and thereafter to be connected by screw thread 105 at its upper section to adapter 24 via internal screw thread 27 in the lower end thereof. The upper portion of the adapter has an external screw thread 25 thereon for a purpose which will later be described. As described above,in the preferred embodiment the stub 102 is made of a light transparent polycarbonate resin material. Stand off ring 22 is preferably made of aluminum, but could be any metal or plastic type material having structural qualities, such as strength and wearability, sufficient for the intended use thereof which will later become apparent. Adapter 24 can be made of the same material as the stand off ring and has an enlarged cylindrical lower section 26 with an internal screw thread 27 in the lower end of the same size as screw thread 105 on stub 102 to cooperatively engage with the latter in use. Stand off ring 22 has a cylindrical hole 23 extending therethrough having a size relative to the outer dimension of section 26 of adapter 24 to receive the latter therein in sliding guiding relationship therewith for supporting the adapter laterally as discussed above, and as clearly shown in the cross-sectional view of FIG. 4.

Figure 4:
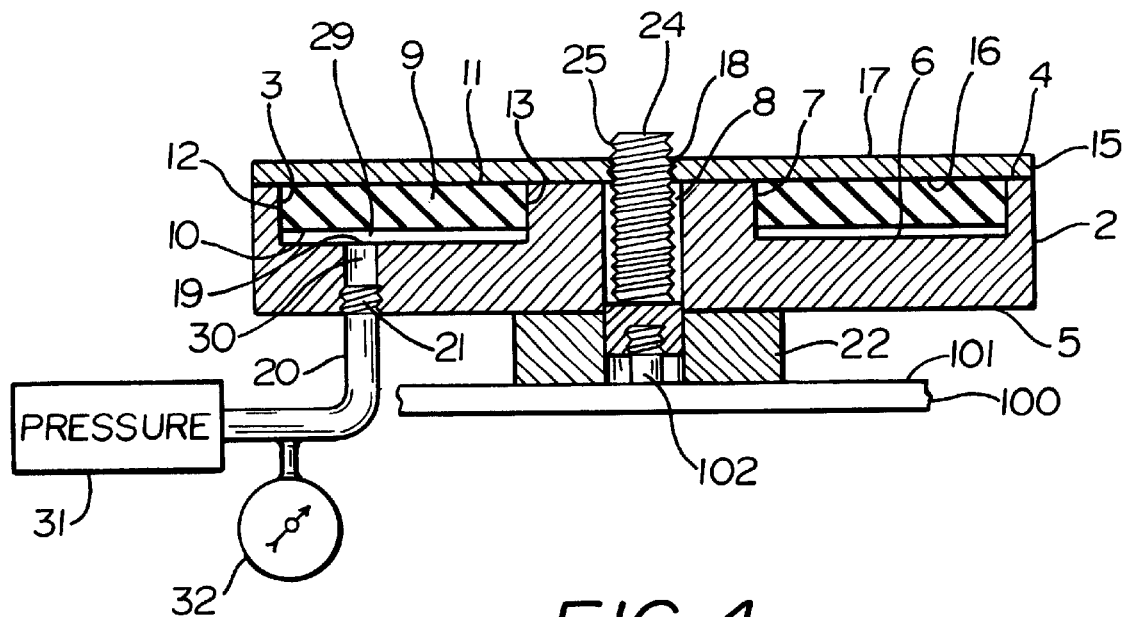
FIG. 4 is a cross-sectional view taken along the line 3—3 of FIG. 3, except that the workpiece is included.
Figure 3:
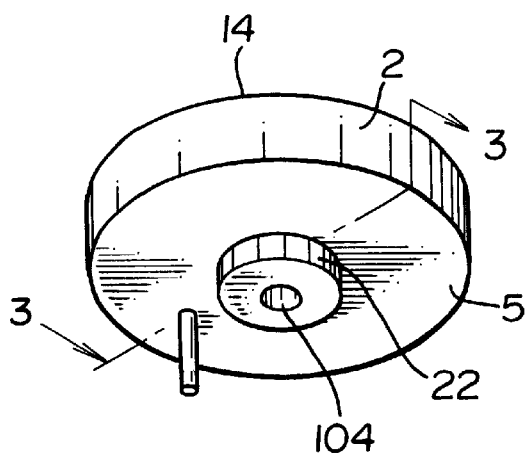
FIG. 3 is a perspective view from the bottom of the apparatus of FIG. 2 when assembled for operation with the workpiece omitted.

The power unit for applying the pulling force on the stub is a piston-cylinder arrangement consisting primarily of cylinder 1, piston 9 and reaction plate 14 all having a common longitudinal axis when assembled as shown in FIG. 4. Cylinder 1 has an outer cylindrical surface 2, an inner cylindrical surface 3, an upper edge, and a lower plate shaped portion having a bottom surface 5 and an upper inner surface 6. An inner cylindrical portion 28 extends upwardly from surface 6 a distance no greater than cylindrical surface 3 to form therewith an inner cylindrical piston cavity to receive piston 9 therein. Cylinder 1 may be made of any machinable material such as aluminum, stainless steel, plastic or other material commonly used with pressurized fluids and suitable for supporting the loads developed in use. Piston 9, which can be made of a compressible silicon compound, has a lower inner surface 10, an upper surface 11, a radially outer or peripheral surface 12, and an aperture 13 for receiving therein the upwardly extending portion of cylinder 1 as better shown in FIG. 4. Outer surface 12 is configured and dimensioned to closely fit in sliding sealing engagement with inner surface 3 and aperture 13 is configured and dimensioned to closely fit in sliding sealing engagement with radially outer cylindrical wall 7 of cylindrical extension 28 to form a sealed chamber 29 between surfaces 6, 10, 7 and 3. As shown in FIG.4, fluid pressure aperture 19 penetrates the lower plate shaped portion of cylinder 1 and has a screw threaded portion 21 for sealingly engaging a cooperating external screw thread 30 on the end of fluid pressure conduit 20, the other end of which is operatively connected to a fluid pressure source 31 for controllably applying fluid pressure to chamber 29. Pressure gage 32 is operatively connected to pressure conduit 20, or pressure source 31, to sense and indicate the pressure applied to chamber 30.

Reaction plate 14, which may be made of the same materials as cylinder 1, has outer peripheral wall portion 15, lower face 16, upper face 17 and a central hole 18 therethrough which has an internal screw thread for cooperatively engaging the upper end of screw thread 25 when the apparatus is assembled for use, as shown in FIG. 4.

The operation of the apparatus of the invention will now be described. With the sample to be tested in place, light curable adhesive is applied as described above between the light transparent stub 102 and coating 101, the high intensity light 106 is position above the stub (FIG. 1) and energized and focused to irradiate and cure the adhesive, using the cut off ring 106 if desired. The light is then removed, as well as the cut off ring if used, and stand off ring 22 is installed over the stub, adapter 24 is inserted through hole 23 and rotated to engage screw thread 27 with screw thread 105 on the stub, and cylinder 1 with piston 9 therein is positioned on the stand off ring with the adapter extending through hole 8 as shown in FIG. 4. The reaction plate 14 is then positioned on top of the cylinder edge 4 and rotated to engage screw thread 18 with screw thread 25 sufficiently to at least secure the piston in the cavity of the cylinder. The pressure source 31 is then operated to apply fluid pressure slowly through conduit 20 into chamber 29 and against elastic and compressible piston 9 which forces the piston to expand against the outer 3 and inner 28 peripheral walls of the cylinder to seal chamber 29 and against the lower surface 16 of the reaction plate to produce a tensile force on adapter 24 and stub 102. The fluid pressure is increased and or controlled to that required for stripping the coating 101 in the test area from substrate 100, or to produce the desired force. The cylinder cavity is formed so that its centroid of transverse area lies on the longitudinal axis common to the piston, adapter, and stub, thereby aligning the force on the stub perpendicular to the surface of the coating 101. The operations and functions of the piston and cylinder device and the sensing and measuring device 32, as well as the type of sensing device, are the same as the force applying device and gage described in the above referred to U.S. Pat. No. 4,567,758.

It will be noted that all embodiments of the present invention provide a unique method and apparatus for testing the bond strength of materials. Although preferred embodiments of the invention have been disclosed, it should be understood that the spirit and scope of the invention is to be limited solely by the appended claims, since modifications may appear to those skilled in the art.

We claim:

1. A method for testing the bond strength of materials, comprising the steps of:

providing a sample consisting of a substrate having a coating bonded to a surface on said substrate;

providing a stub member that is at least partly transparent to light having a surface thereon to be affixed to a test area of said coating;

applying a layer of light curable adhesive between said surface on said stub and said test area;

irradiating said adhesive with light applied through said stub member to cure said adhesive and thereby affix said stub member to said test area;

applying a force to said stub member in a direction substantially normal to said coating for separating said coating from said substrate in said test area; and measuring the force required to produce said separation and to determine the strength of the bond between said coating and said substrate.

2. The method as claimed in claim 1 wherein said step of providing a stub member that is at least partly transparent to light comprises:

providing a stub member of a fully light transparent material.

3. The method as claimed in claim 1 wherein said irradiating step comprises:

positioning a high intensity light source so that said stub is between said light source and said test area; and irradiating said adhesive for a time sufficient to cure said adhesive.

4. The method as claimed in claim 3 wherein said irradiating comprises:

providing a cut off ring having an internal diameter slightly larger than the outer diameter of said stub;

irradiating said adhesive for about 30 seconds;

placing said cut off ring on said stub in contact with said adhesive;

irradiating said adhesive again for about 30 seconds; and removing said cut off ring from said stub.

5. The method as claimed in claim 1 and further comprising:

laterally supporting and guiding said force for maintaining said force substantially normal to said coating.

6. The method as claimed in claim 2 and further comprising;

laterally supporting and guiding said force for maintaining said force substantially normal to said coating.

7. The method as claimed in claim 4 and further comprising:

laterally supporting and guiding said force for maintaining said force substantially normal to said coating.

8. Apparatus for testing the bond strength of a material bonded to a substrate comprising:

a stub member of material that is at least partly transparent to light having a surface thereon attachable to a test area on said material being tested by a light curable adhesive;

light source means removably positionable in relation to said stub member and said adhesive for irradiating said adhesive through said stub member for curing and bonding said stub member to said test area;

piston and cylinder means connectable to said stub member for aplying a force to said stub member in a direction substantially normal to said test area;

adapter means for connecting said stub member to said piston and cylinder means;

fluid pressure means operatively connected to said piston and cylinder means for actuating said piston and cylinder means; and sensing means for sensing and indicating pressure applied to said piston and cylinder means by said fluid pressure means.

9. The apparatus as claimed in claim 8 and further comprising:

stand off ring means positionable between said material being tested and said piston and cylinder means for laterally supporting and guiding said adapter means during application of said force by said piston and cylinder means to maintain said force on said stub member in said direction substantially normal to said test area.

10. The apparatus as claimed in claim 8 wherein said piston and cylinder means comprises:

a cylinder housing having a lower end plate, a longitudinal axis, an outer peripheral region on said end plate, an outer cylindrical cylinder wall extending axially from said outer peripheral region on said end plate, a central cylindrical hub extending axially from said end plate, an inner cylindrical cylinder wail on said hub spaced radially inwardly from said outer cylinder wall thereby forming an annular piston cavity, and an aperture extending axially through said hub for receiving said adapter means freely movable therein;

an annular piston of compressible material in said cavity having an outer peripheral surface in sliding sealing engagement with said outer cylinder wall and a radially inner surface in sliding sealing engagement with said inner cylinder wall forming a compression chamber between said piston, said lower end plate, and said cylinder walls;

fluid communication means extending through said housing communicating with said chamber;

an upper reaction plate having a radially outer peripheral portion extending radially outwardly of said cavity, and a central hole therethrough for receiving said adapter means in engagement therewith; and means for connecting said fluid pressure means to said fluid communication means so that fluid pressure from said fluid pressure means is fed to said compression chamber forcing said piston axially against said reaction plate and radially against said inner and outer cylinder walls to apply said force to said stub member.

11. The apparatus as claimed in claim 10 wherein:

said stub member comprises a screw threaded portion extending in a direction substantially normal to said test area;

said adapter means comprises an elongated member extending substantially normal to said test area having a cylindrical end, an internal screw threaded portion in said cylindrical end cooperatively engageable with said screw threaded portion on said stub member, and an external screw threaded portion for connecting said adapter to said piston and cylinder means, and further comprising;

a stand off ring having a first surface engageable with said material being tested around said test area, a second surface engageable with said lower end plate of said cylinder housing, and a hole therethrough for receiving said cylindrical end of said adapter means in sliding guiding relationship to laterally support said adapter means for maintaining said force on said stub member in said direction substantially normal to said test area during application of said force by said piston and cylinder means; and an internal screw thread in said central hole in said reaction plate for cooperatively engaging with said external threaded portion on said adapter means for clamping said piston and cylinder means in substantially fixed spaced relationship with respect to said material being tested.

12. The apparatus as claimed in claim 8 wherein:

said stub member is made of light transparent material.

13. The apparatus as claimed in claim 8 wherein:

said stub member is made of metal; and a bore extends therethrough for transmitting light.

14. The apparatus as claimed in claim 11 wherein:

said stub member is made of fully light transparent material.

15. The apparatus as claimed in claim 11 wherein:

said stub member is made of metal; and a bore extends therethrough for transmitting light.

\* \* \* \* \*